United States Patent
Painchaud et al.

(10) Patent No.: US 11,344,712 B2
(45) Date of Patent: May 31, 2022

(54) IMPLANT INJECTION DEVICE HAVING A RACK AND PINION TRANSMISSION

(71) Applicant: Nemera La Verpillière, La Verpilliere (FR)

(72) Inventors: Gaëtan Painchaud, Francheville (FR); Pascal Dugand, Estrablin (FR); Thomas Megard, La Roche-Vineuse (FR)

(73) Assignee: Nemera La Verpillière

( * ) Notice: Subject to any disclaimer, the term of this patent is extended or adjusted under 35 U.S.C. 154(b) by 12 days.

(21) Appl. No.: 16/387,109

(22) Filed: Apr. 17, 2019

(65) Prior Publication Data

US 2019/0321075 A1 Oct. 24, 2019

(30) Foreign Application Priority Data

Apr. 18, 2018 (FR) ...................................... 1853406

(51) Int. Cl.
*A61M 37/00* (2006.01)
*A61B 17/34* (2006.01)
*A61F 2/00* (2006.01)
*A61M 5/50* (2006.01)
*A61M 5/32* (2006.01)
*A61B 90/00* (2016.01)

(52) U.S. Cl.
CPC ..... *A61M 37/0069* (2013.01); *A61B 17/3468* (2013.01); *A61F 2/0095* (2013.01);
(Continued)

(58) Field of Classification Search
CPC ................ A61B 17/3468; A61B 90/98; A61B 2090/034; A61B 2090/3987; A61B 2017/347; A61B 2090/0814; A61M 37/0069; A61M 5/322; A61M 5/315; A61M 5/31565; A61M 5/31576; A61M 5/3157; A61M 5/31578; A61M 2205/581; A61M 5/31526; A61M 5/31528; A61M 5/50; A61M 5/5086; A61M 2202/06;
(Continued)

(56) References Cited

U.S. PATENT DOCUMENTS 2,883,984 A * 4/1959 Candido, Jr. ..... A61M 37/0069
604/61
4,447,223 A 5/1984 Kaye et al.
(Continued)

FOREIGN PATENT DOCUMENTS

EP 2719355 A2 * 4/2014 ......... A61B 17/3468
EP 2719355 A2 4/2014
(Continued)

*Primary Examiner* — Shefali D Patel
(74) *Attorney, Agent, or Firm* — St. Onge Steward Johnston & Reens LLC

(57) ABSTRACT

An implant injection device, including an injection needle, a receiver housing for receiving at least one implant, an injection mechanism, the injection mechanism including a pushing rod, arranged upstream from the at least one implant housed in the receiver housing, extending longitudinally and configured to push the at least one implant through the injection needle between an initial position and a final position in which the at least one implant is injected, a mechanism for actuation by a user, configured to actuate a displacement of the pushing rod from the initial position to the final position, the mechanism for actuation including a rack transmission mechanism.

11 Claims, 3 Drawing Sheets

(52) U.S. Cl.
CPC ............ *A61M 5/50* (2013.01); *A61M 5/5086* (2013.01); *A61B 2017/347* (2013.01); *A61B 2090/0814* (2016.02); *A61M 5/322* (2013.01); *A61M 2205/273* (2013.01); *A61M 2205/581* (2013.01); *A61M 2205/582* (2013.01)

(58) Field of Classification Search
CPC ........ A61M 2205/27; A61M 2205/273; A61M 2205/582; A61F 9/0017; A61F 2/0095
USPC ................................ 604/60, 57, 59, 62, 110
See application file for complete search history.

(56) References Cited

U.S. PATENT DOCUMENTS

| | | | | |
|---|---|---|---|---|
| 4,474,572 A | * | 10/1984 | McNaughton | A61M 37/0069 604/61 |
| 4,576,591 A | | 3/1986 | Kaye et al. | |
| 4,762,515 A | * | 8/1988 | Grimm | A61M 37/0069 604/61 |
| 2009/0281520 A1 | * | 11/2009 | Highley | A61F 9/0017 604/506 |
| 2010/0137791 A1 | * | 6/2010 | Plumptre | A61M 5/31555 604/68 |
| 2015/0051551 A1 | * | 2/2015 | Hirschel | A61M 5/31585 604/189 |
| 2016/0296739 A1 | * | 10/2016 | Cleveland | A61M 5/31526 |
| 2018/0001032 A1 | * | 1/2018 | Kleyman | A61M 5/31578 |
| 2019/0298930 A1 | * | 10/2019 | Morris | A61M 5/31583 |

FOREIGN PATENT DOCUMENTS

| | | | | |
|---|---|---|---|---|
| EP | 3210573 A1 | * | 8/2017 | ........ A61M 5/31581 |
| WO | 2004026106 A2 | | 4/2004 | |
| WO | WO-2004026106 A2 | * | 4/2004 | ........ A61M 37/0069 |
| WO | 2006071554 A2 | | 7/2006 | |
| WO | WO-2017147722 A1 | * | 9/2017 | ............. A61F 2/167 |

* cited by examiner

IMPLANT INJECTION DEVICE HAVING A RACK AND PINION TRANSMISSION

FIELD OF THE INVENTION

The invention relates to the technical field of injecting one or more implants into a patient's body.

BACKGROUND OF THE INVENTION

Implant injection devices, comprising a hollow needle attached to a housing receiving an implant, are known. The implant is injected using a pushing rod, which pushes the implant through the hollow needle then beyond to inject the implant into a patient's body.

In particular, document US20090281520A1 describes an implant injection device in which the implant can be injected by slidably pressing a button, the button then being pressed by the user in a direction substantially parallel to the injection direction. Thus, before actuation, the pushing rod is retracted and the button is located on the side of the proximal end of the device, in other words the end opposite the injection end. When the user slidably presses the button, the button slides in a direction substantially parallel to the injection direction and moves the pushing rod, which pushes the implant and allows its injection.

However, with such actuation by slidably pressing, the user is unable to inject several implants easily. This actuation is generally carried out by the user's thumb, which has a limited actuation stroke that is insufficient for the stroke required to inject a very long implant and/or for the successive injection of two or more implants. In addition, with such actuation, good injection accuracy cannot be maintained over a long stroke and in particular the injection cannot be stopped once the implant has been injected, for example to direct the injection needle in another direction for a second implant to avoid injecting too deeply. With such actuation, there is in fact a risk of accidentally starting to inject an implant after the implant already injected. This is not desirable to guarantee correct injection, in particular to avoid breaking at least one of the implants or injuring the patient.

Thus, in view of their actuation type, these implant injection devices cannot be used to easily inject a very long implant or a plurality of implants.

SUMMARY OF THE INVENTION

This invention aims in particular to provide an implant injection device which can be used to easily inject a very long implant and/or a plurality of implants. Thus, the invention relates in particular to an implant injection device comprising:
  an injection needle,
  a receiver housing for receiving at least one implant,
  injection means, the injection means comprising:
    a pushing rod, arranged upstream from the implant housed in the receiver housing, extending longitudinally and configured to push the implant through the injection needle between an initial position and a final position in which the implant is injected,
    means for actuation by a user, configured to actuate a displacement of the pushing rod from the initial position to the final position, the actuation means comprising a rack transmission mechanism.

Thus, it is proposed to produce an implant injector that is easy to handle and to assemble, by creating a transmission of movement that is pleasant for a user. Through one or more movements of small amplitude, the user can in fact actuate the pushing rod over a long distance using the rack transmission, in order for example to inject a very long implant or a plurality of implants.

It is understood that a rack transmission mechanism preferably comprises a straight toothed element cooperating with a gear to transform a rotation movement into a translation movement or vice versa.

An "implant" is preferably understood to mean a pharmaceutical compound in solid or semi-solid state, for example in the form of an encapsulated liquid and/or an electronic component, for example an RFID type electronic chip. A "patient" or "subject" is generally understood to mean a living being, for example a mammal, in particular a human being. The user is generally a person different from the patient but the user may be the patient himself.

In this description, it is understood that the distal direction designates the direction farthest away from a user's fingers, in other words closest to the skin or the surface of a patient at the time of an injection, and the proximal direction designates the direction opposite to the distal direction. In other words, it is considered that the distal direction and the distal sense are the direction and sense which go towards the "front" of the implant injection device, the direction also called the injection direction. In particular, the distal end of a part corresponds to the end located on the side of the injection needle and the proximal end corresponds to the opposite end. It is also understood that the injection axis, which is the injection direction, corresponds to the axis of the implant injection device defined by the axis of the injection needle.

Consequently, it is understood that the "downstream" direction is a direction opposite to the "upstream" direction and corresponds to the direction towards the distal end of the implant injection device, in other words towards the injection site, towards the end configured to be in contact with the implant injection site. Thus, the "downstream" direction may also be called the injection direction.

It is understood that the terms "upstream" and "downstream" designate the distal and proximal directions, respectively, a downstream element being arranged further away in the distal direction than an upstream element. The implant injection device may further comprise one or more of the following characteristics, taken alone or in combination.

The rack transmission mechanism comprises a first rack element and a second rack element,
  the first rack element being configured to be driven by the user and forming a first rack and pinion type link with a pinion, the pinion comprising a first set of gear teeth cooperating with the first rack element,
  the pinion comprising a second set of gear teeth cooperating with the second rack element, configured to push the pushing rod from the initial position to the final position.

Thus, a rack transmission mechanism comprising a pinion and two rack elements is proposed, to multiply the user's movement. In other words, by a sliding movement over a short distance, driving the first rack element, the user can actuate the pushing rod over a long distance, in order for example to inject a very long implant or a plurality of implants. Advantageously, the first and second sets of gear teeth of the pinion consist of a first gear and a second gear of the pinion, the diameter of the first gear being less than the diameter of the second gear.

The actuation means comprise an actuation button sliding in a direction substantially parallel to the longitudinal direction of the pushing rod, which is supported by the first rack element. Thus, the movement required to actuate the implant injection device is especially easy for a user, who can for example easily hold the implant injection device in one hand and actuate the pushing rod using the sliding actuation button, with the thumb of this hand.

The implant injection device comprises means for indicating a position of the pushing rod to the user. Thus, the user can easily check the position of the pushing rod and can, for example, stop actuating the pushing rod by using the indication supplied by the indication means, which is especially advantageous if a position corresponding to the end of injection of a first implant is indicated. This indicates to the user that he can remove the implant injection device or change the injection direction to inject a second implant at the same depth as the first implant.

The indication means comprise a first flexible tab carried by a unit, and the rack transmission mechanism comprising at least one projection, such that when the rack transmission mechanism reaches a first predetermined position, the projection is in abutment against the first flexible tab to give the user a first audible and/or tactile indication. Thus, when the rack transmission mechanism reaches a first predetermined position, the user detects via the audible and/or tactile indication, which is especially practical, that the rack transmission mechanism has reached this first predetermined position, which may, for example, correspond to a position in which an implant is injected. This can be used, for example, to indicate to the user that he must stop the injection when the injection of an implant is complete, for example to avoid injecting too deeply or to direct the injection needle in another direction for a subsequent implant such as a second implant, to avoid injecting too deeply.

The indication means comprise a second flexible tab carried by the unit, the second flexible tab being configured to abut against the projection in a second predetermined position preceding the first predetermined position, such that when the rack transmission mechanism reaches a second predetermined position, the projection is in abutment against the second flexible tab, and when the rack transmission mechanism goes past the second predetermined position, the second flexible tab crosses the projection in order to give the user a second audible and/or tactile indication. Thus, when the rack transmission mechanism reaches a second predetermined position, which corresponds to a position preceding the first predetermined position, the user detects via the audible and/or tactile indication that the rack transmission mechanism has reached this second predetermined position, which may, for example, correspond to a position preceding a position in which an implant is injected. This can be used for example to indicate to the user to slow down the injection when the injection of an implant is almost complete, to avoid injecting too deeply.

The bending strength of the first flexible tab is greater than that of the second flexible tab. Thus, the tactile and/or audible indication is different depending on whether the rack transmission mechanism has reached the second predetermined position or the first predetermined position. The second predetermined position may correspond to an intermediate actuation position in which a part of implant is still to be injected, and the first predetermined position may correspond to an actuation position in which an implant is injected. It is therefore useful that the bending strength of the first flexible tab should be greater than that of the second flexible tab, thereby allowing the user to easily detect that the implant is injected, to avoid injecting too deeply, or to direct the injection needle in another direction for a subsequent implant such as a second implant, to avoid injecting too deeply.

The receiver housing is adapted to receive a plurality of implants, the pushing rod, in the first predetermined position of the rack transmission mechanism, occupies a position in which an implant is injected. Thus, the user easily detects than the implant is injected, to avoid injecting too deeply, or to direct the injection needle in another direction for another implant, to avoid injecting too deeply.

The at least one projection comprises a tooth protruding from a flat longitudinal surface of the rack transmission mechanism. Thus, the indication means are extremely easy to produce.

The implant injection device comprises a unit, the pinion being pivotally mounted on the unit. Thus, the rack transmission mechanism is extremely easy to produce.

The number of teeth of the first set of gear teeth is strictly less than the number of teeth of the second set of gear teeth. Thus, multiplication of the user's movement is extremely easy to produce. In addition, for example, the number of teeth of the first set of gear teeth is between 5 and 15, preferably between 5 and 10, more preferably close to or equal to 5; and/or the number of teeth of the second set of gear teeth is between 6 and 30, preferably between 16 and 25, more preferably close to or equal to 18.

The ratio of the displacement of the second rack element to the displacement of the first rack element is between 2 and 10, preferably between 3 and 5, more preferably close to or equal to 3.6. Thus, multiplication of the user's movement is optimized. If the ratio of the displacement of the second rack element to the displacement of the first rack element is too high, the injection accuracy is affected, and if the ratio of the displacement of the second rack element to the displacement of the first rack element is too low, the amplitude of the movement to be produced for actuation by the user is too high.

The implant injection device comprises locking means arranged to block the pushing rod in its final position, position in which the pushing rod preferably projects towards the downstream direction past the end of the injection needle. Thus, the implant injection device is not reusable, thereby respecting hygiene constraints relating to this type of implant injection device. In addition, when in its final position, the pushing rod projects towards the downstream direction past the end of the injection needle, the pushing rod forms in this case a safety element for the end of the injection needle which may be beveled for easier insertion into the skin. The pushing rod can then prevent the needle from exerting its insertion function, for example on a person or an object if the implant injection device is dropped. Thus, if the implant injection device is dropped or pressed in the distal direction, the contact with the implant injection device is made via the pushing rod and not with the end of the injection needle.

BRIEF DESCRIPTION OF THE DRAWINGS

It will be easier to understand the invention on reading the description below, given as an example and referring to the drawings, on which.

DETAILED DESCRIPTION OF THE INVENTION

Figure 1:
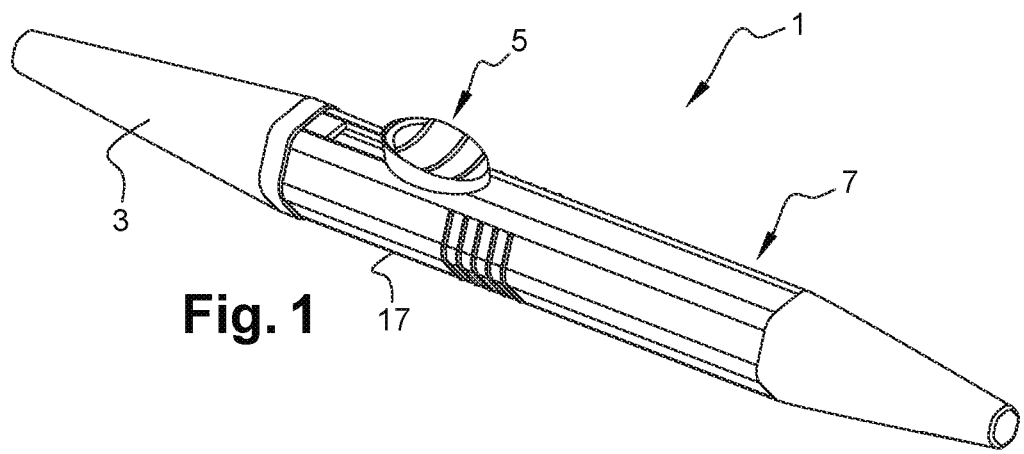
FIG. 1 is a perspective view of an implant injection device according to one embodiment, in storage configuration before injection.
Figure 2:
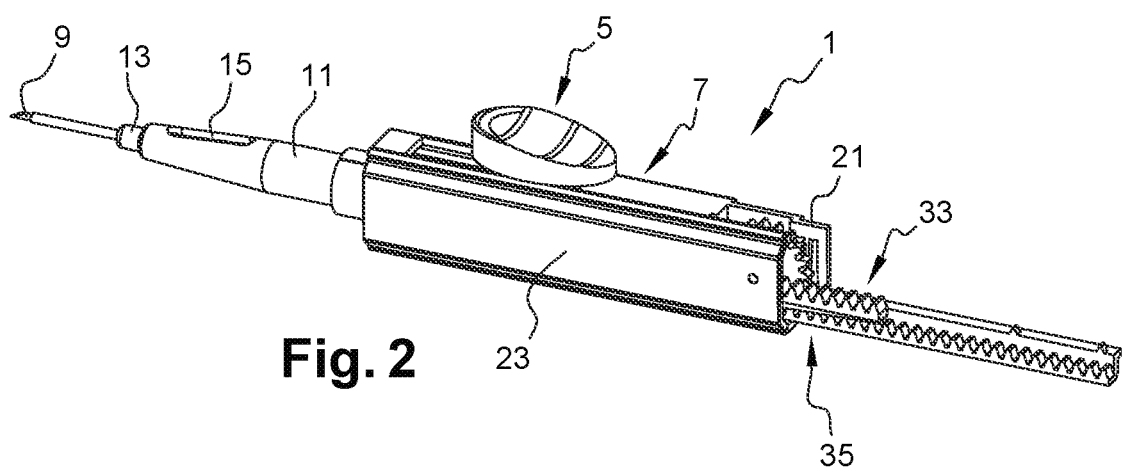
FIGS. 2 and 3 are side and perspective views of a part of an implant injection device of FIG. 1, in which the pushing rod is in an initial position.

As shown on FIGS. 1 and 2, an implant injection device 1 comprises an injection needle 9 (shown on FIG. 2) carried by a gripping unit 7 and protected by a cap 3 (shown on FIG. 1), a receiver housing 11 (shown on FIG. 2), for receiving at least one implant, injection means 5 and a gripping unit 7.

The implant injection device 1 is configured to inject one or more implants into a patient's body via the injection needle 9 shown. Although in the remainder of the document, the example is illustrated with two implants, the implant injection device 1 can also apply to a single implant, or a number of implants greater than two, such as for example three, four, five, ten implants.

Figure 6:
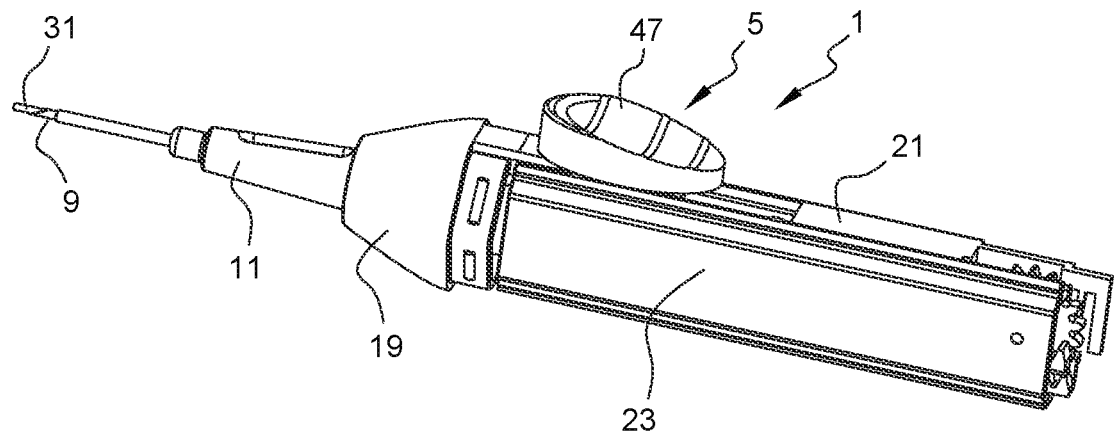

As shown on FIGS. 2 and 6, the injection needle 9 is hollow and is for example made of metal such as stainless steel. The injection needle 9 comprises a beveled distal end for easier insertion into the patient's body. The injection needle 9 carries a support element 13, which can be made from plastic and is intended to limit the depth of insertion of the injection needle 9 into the patient's body. The injection needle 9 is attached at its proximal end to the receiver housing 11. It can be protected in storage configuration by the cap 3.

The cap 3 is a cap protecting the injection needle 9, in this case it is assembled on the gripping unit 7, by clipping its proximal end to the gripping unit 7. However, other assembly means are possible, for example by screwing. In this example, the cap 3 is bullet-shaped and can be provided with reliefs for easier gripping.

The receiver housing 11 is a housing for receiving two implants. As shown on FIG. 2, the receiver housing 11 has a generally tubular and/or frustoconical shape, and houses the implants in its internal space, such that the implants are directed towards the end of the injection needle 9, opposite the proximal end of the injection needle 9. In other words, the receiver housing 11 is arranged upstream from the injection needle 9, and is intended to receive the implants such that the implants are arranged upstream from the injection needle 9, in the injection direction of the injection needle 9. The receiver housing 11 is configured to contain two implants, the two implants being arranged one behind the other, in other words one upstream from the other, in the injection direction. The receiver housing 11 may comprise, at its distal end, an implant retaining means, such as a membrane or a slight narrowing of its inner diameter, intended to prevent an implant from falling through the injection needle 9, for example under the effect of the force of gravity. The receiver housing 11 may also comprise, at its distal end, a flexible implant retaining element comprising an orifice of diameter less than that of the implants, the orifice being configured to deform and allow the implants to pass towards the injection needle 9 during the injection. The receiver housing 11 advantageously comprises a window 15 (shown on FIG. 2). Thus, a user can detect visually, through the window 15, the presence of the implants in the implant injection device 1, before performing the injection on a patient, after removing the cap 3. Note that in this example, the injection needle 9 and the receiver housing 11 are parts attached to each other, but that it would nevertheless be possible to consider that the injection needle 9 and the receiver housing 11 should form two portions of the same part, for example by being made in one piece. In addition, the receiver housing 11 is attached at its proximal end to the gripping unit 7, for example by clipping its proximal end to the gripping unit 7, as shown on FIG. 3. The receiver housing 11 thus comprises a peripheral rib 16, which engages in a corresponding groove 18 carried by the gripping unit 7. However, other assembly means are possible, for example by screwing. Alternatively, the receiver housing 11 could be formed directly in the gripping unit 7, being made in one piece with it. In this example, the receiver housing 11 is made of plastic, possibly transparent.

In the example shown, the gripping unit 7 consists of several elements:
- an outer portion, composed of an outer gripping element 17 (shown on FIG. 1) of generally tubular shape, and a distal plug 19 (shown on FIG. 6), and
- an inner portion, composed of two support elements 21, 23 for supporting the injection means 5 assembled together, in other words a male support element 21 and a female support element 23 (shown on FIG. 2).

Figure 7:
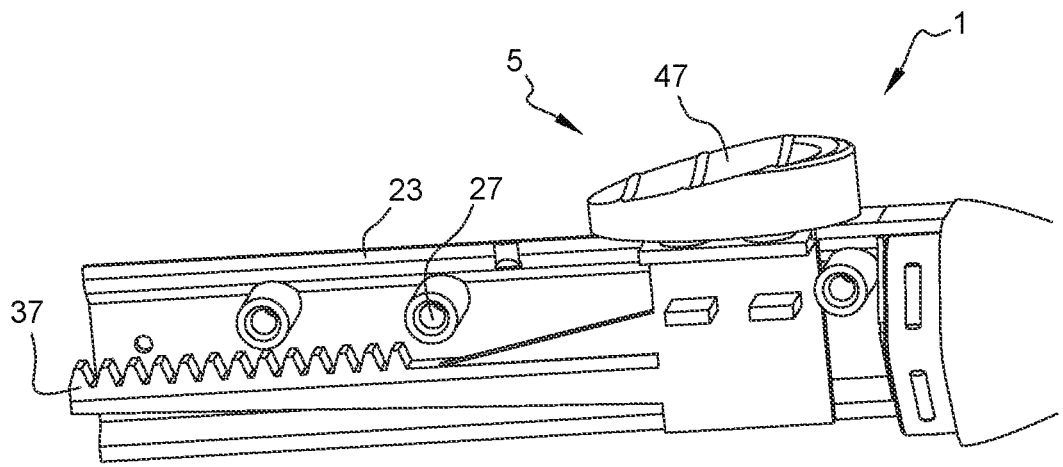

In the assembled state, the outer gripping element, the distal plug 19 and the two support elements 21, 23 are held in position relative to one another. Thus, the two support elements 21, 23 are assembled by clipping pins 25 (shown on FIG. 3) carried by the male support element 21 in tubular housings 27 (shown on FIG. 7) carried by the female support element 23. In addition, in the assembled state, the distal plug 19 is in abutment against the distal end of the two support elements 21, 23, and is assembled to the outer gripping element 17 by clipping projections 29, such as for example semi-cylindrical sections as shown on FIG. 5, in a corresponding inner peripheral groove of the outer gripping element 17.

The injection means 5 are used to push the one or more implants through the injection needle 9 between an initial position and a final position in which the one or more implants are injected. As shown in particular on FIG. 3, the injection means 5 comprise a pushing rod 31 and means 33 for actuation by a user.

The pushing rod 31 is arranged upstream from the implants housed in the receiver housing. The pushing rod 31 extends longitudinally and is configured to push the implants through the injection needle 9 between an initial position and a final position in which the implants are injected.

The pushing rod 31 can be made of metal, for example steel, preferably stainless steel. The pushing rod 31 is arranged upstream from an implant which is itself the implant being arranged in the most upstream position of the implants. The pushing rod 31 is therefore configured to push the implant, in this case the implants, through the injection needle 9 between an initial position and a final position. Thus, in the initial position of the pushing rod 31, the implants are housed in the receiver housing 11, and in the final position of the pushing rod 31, the implants have passed through the injection needle 9 and are a priori placed in a patient's body.

The means 33 for actuation by a user are configured to actuate a displacement of the pushing rod 31 from the initial position to the final position. The actuation means 33 comprise a rack transmission mechanism 35.

Figure 3:
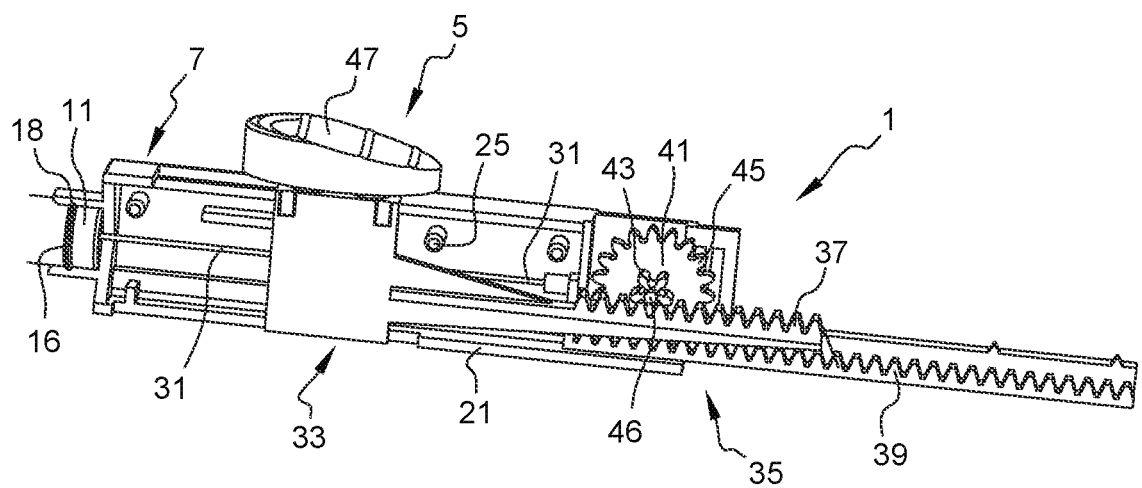

As shown on FIG. 3, the rack transmission mechanism 35 comprises a first rack element 37 and a second rack element 39.

The first rack element 37 is a driving rack element. It is thus configured to be driven by the user and forms a first rack and pinion type link with a pinion 41.

As shown on FIG. 3, the pinion 41 comprises a first set of gear teeth 43 cooperating with the first rack element 37, and the pinion 41 comprises a second set of gear teeth 45 cooperating with the second rack element 39 configured to push the pushing rod 31 from the initial position to the final position. The pinion 41 thus forms a second rack and pinion type link with the second rack element 39. The first 43 and second 45 sets of gear teeth of the pinion 41 consist respectively of a first gear 43 and a second gear 45, the diameter of the first gear 43 being less than the diameter of the second gear 45.

The number of teeth of the first set of gear teeth 43 is strictly less than the number of teeth of the second set of gear teeth 45, to multiply the movement. For example, the number of teeth of the first set of gear teeth 43 is between 5 and 15, preferably between 5 and 10, more preferably close to or equal to 5, and/or the number of teeth of the second set of gear teeth 45 is between 6 and 30, preferably between 16 and 25, more preferably close to or equal to 18. The number of teeth of the first set of gear teeth 43 and the number of teeth of the second set of gear teeth 45 are preferably chosen so that the ratio of the displacement of the second rack element 39 to the displacement of the first rack element 37 is between 2 and 10, preferably between 3 and 5, more preferably close to or equal to 3.6.

The pinion 41 is pivotally mounted in the gripping unit 7. The pinion 41 therefore comprises a trunnion at each end, one trunnion being carried by the male support element 21, and one trunnion 46 being carried by the female support element 23. The axis of rotation of the pinion 41 is substantially orthogonal to the longitudinal direction of the pushing rod 31, so that the movement of the second rack element 39 can push the pushing rod 31 from the initial position to the final position.

The first rack element 37 further supports an actuation button 47 which is configured to be pressed directly by the user. The actuation button 47 is assembled on the first rack element 37, for example by clipping. It is understood that the first rack element 37 is made in one piece with the actuation button 47.

The actuation button 47 is mounted slidably in a direction substantially parallel to the longitudinal direction of the pushing rod 31. The first rack element 37 and the assembly formed by the male support element 21 and the female support element 23 therefore form a sliding connection between them, in the longitudinal direction of the pushing rod 31.

The second rack element 39 is a driven rack element. It is thus configured to be driven by the pinion 41 and forms a second rack and pinion type link with the pinion 41. The second rack element 39 supports the pushing rod 31, the pushing rod 31 being for example attached by clamping in a housing of the second rack element 39. Thus, when the second rack element 39 is driven, it pushes the pushing rod 31 in the injection direction, from the initial position to the final position.

The second rack element 39 is mounted slidably in a direction substantially parallel to the longitudinal direction of the pushing rod 31. The second rack element 39 and the assembly formed by the male support element 21 and the female support element 23 therefore form a sliding connection between them, in the longitudinal direction of the pushing rod 31. Thus, when it is driven by the pinion 41, the second rack element 39 slides in the longitudinal direction of the pushing rod, causing the pushing rod 31 to move in the distal direction. The pushing rod 31 then pushes at least one implant through the injection needle 9. When the pushing rod 31 is in its final position, the second rack element 39 does not continue its stroke. The gripping unit 7 then forms, in particular via the male support element 21, an abutment for the second rack element 39. Thus, the user cannot inject an implant too deeply, which could injure the patient.

Figure 4:
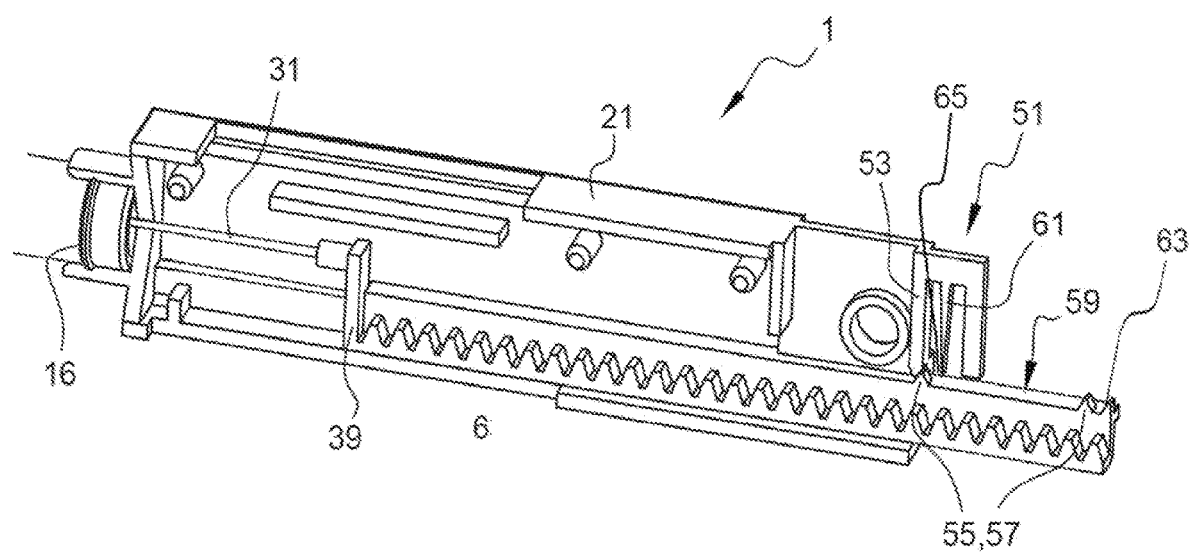
FIG. 4 is a side and perspective view of a part of the implant injection device of FIG. 1, in which the pushing rod is in an intermediate position.

The implant injection device 1 also comprises means 51 for indicating a position of the pushing rod 31 to the user, as shown for example on FIG. 4.

The indication means 51 comprise in this case a first flexible tab 53 carried by the gripping unit 7, in particular by the male support element 21. The rack transmission mechanism 35 comprises at least one projection 55, such that when the rack transmission mechanism 35 reaches a first predetermined position, the projection 55 is in abutment against the first flexible tab 53 to give the user a first audible and/or tactile indication. In the example shown, the pushing rod 31, in this first predetermined position of the rack transmission mechanism 35, occupies a position in which an implant is injected.

In the example shown, in particular on FIG. 4, the first flexible tab 53 is supported by the male support element 21 of the gripping unit 7. The second rack element 39 supports two projections 55, which each comprise a tooth 57 protruding from a flat longitudinal surface 59 of the rack transmission mechanism 35. "Longitudinal surface" may mean a surface extending substantially parallel to the longitudinal surface of the pushing rod 31. In the example shown, the flat longitudinal surface 59 is carried by the second rack element 39.

When the rack transmission mechanism 35 reaches a first predetermined position, for example a position in which an implant is injected, or even an intermediate position in which a first implant is injected and a second implant is not injected and is still inside the implant injection device 1, as shown on FIG. 4, the projection 55 or tooth 57 is in abutment against the first flexible tab 53. In the case of an intermediate position, to inject the second implant, the user must exert a force to deform the first flexible tab 53 and allow a projection 55 or a tooth 57 to cross the first flexible tab 53.

The indication means 51 comprise a second flexible tab 61 carried by the gripping unit 7, in particular by the male support element 21.

The second flexible tab 61 is configured to abut against a projection 55 or tooth 57 in a second predetermined position preceding the first predetermined position.

When the rack transmission mechanism 35 reaches a second predetermined position, for example a position in which an implant is partially injected, even a position in which an implant is almost totally injected, the projection 55 or tooth 57 is in abutment against the second flexible tab 61, and when the rack transmission mechanism 35 goes past the second predetermined position, the second flexible tab 61 crosses the projection 55 or tooth 57 in order to give the user a second audible and/or tactile indication. In this second predetermined position, in order to continue injecting an implant, the user must exert a force to deform the second flexible tab 61 and allow a projection 55 or a tooth 57 to cross the second flexible tab 61.

The bending strength of the first flexible tab 53 is greater than that of the second flexible tab 61. Thus, the user easily distinguishes between the first predetermined position and the second predetermined position. When injecting an implant, the second predetermined position will be reached first, indicating for example to the user that the implant is almost totally injected. Then, the first predetermined position is reached, indicating for example to the user that the implant has been totally injected. This may, for example, allow the user to reposition the implant injection device 1, in particular the injection needle 9, in order to start injecting another implant with a suitable position.

In the example shown, the implant injection device 1 comprising two projections 55 or teeth 57, the rack transmission mechanism 35 may thus occupy two first predetermined positions, respectively two second predetermined positions. In particular, a first predetermined position and a second predetermined position are reached when injecting each of the two implants.

The implant injection device 1 comprises locking means arranged to block the pushing rod 31 in its final position, position in which the pushing rod 31 preferably projects towards the downstream direction past the end of the injection needle 9.

In addition, the implant injection device 1 may comprise locking means arranged to block the pushing rod 31 in the final position. Thus, in this final position, a lug 63 supported by the first rack element 37 or the second rack element 39 cooperates with a recess 65 carried by the gripping unit 7, in particular formed in the male support element 21. Advantageously, the lug 63 can be formed on the longitudinal surface 59 of the second rack element 39 and take the form of a ramp 63 ending at its upstream end with a wall substantially orthogonal to the longitudinal surface, such that when the first flexible tab 53 or the second flexible tab 61 crosses this ramp, an audible signal such as a "click" can be heard by the user. In addition, the presence of the substantially orthogonal wall prevents the lug from being crossed in the other direction, except for example by breaking the first flexible tab 53 or the second flexible tab 61. This is a simple way of preventing the implant injection device 1 from being reused and also prevents injury due to the injection needle 9, for example if the implant injection device 1 is dropped after use, since the pushing rod 31 projects past the end of the injection needle 9 and is blocked by these locking means.

The elements of the implant injection device 1, whose material is not specified in this description, may be made from a thermoplastic material, for example polyethylene or polypropylene.

An example of operation of the implant injection device 1 will now be described.

The implant injection device 1 as shown on FIG. 1 is in storage configuration before use.

The user must remove the cap 3 protecting the injection needle 9, as shown on FIG. 2—the implant injection device 1 being considered to be assembled—and check that the one or more implants are present by looking through the window 15 of the receiver housing 11.

The injection needle 9 is then inserted into the patient's body and the user slides the actuation button 47. The actuation button 47 and the first rack element 37 then slide relative to the gripping unit 7. The first rack element 37 then drives the pinion 41 in rotation via its first set of gear teeth 43. Rotation of the pinion 41, via its second set of gear teeth 45 in contact with the second rack element 39, causes the second rack element 39 to slide. The second rack element 39 then pushes the pushing rod 31 in the injection direction, from its initial position to its final position. The pushing rod 31 then pushes the one or more implants through the injection needle 9 to inject the one or more implants into the patient's body.

Then, when the rack transmission mechanism 35 reaches a second predetermined position, for example a position in which an injection of an implant is almost complete, the projection 55 or tooth 57 is in abutment against the second flexible tab 61. If the user continues to press the actuation button 47, he must then exert a force so that the rack transmission mechanism 35 goes past the second predetermined position. This deforms the second flexible tab 61 and allows the second flexible tab 61 to cross the projection 55 or tooth 57 in order to give the user a second audible indication such as a "click" and/or tactile indication, due for example to the extra force required to cross the projection 55 or tooth 57.

Then, when the rack transmission mechanism reaches a first predetermined position, for example a position in which the pushing rod 31 occupies a position in which an implant is injected, as shown on FIG. 4, the projection 55 or tooth 57 is in abutment against the first flexible tab 53. If the user continues to press the actuation button 47, he must then exert a force so that the rack transmission mechanism 35 goes past the first predetermined position. This deforms the first flexible tab 53 and allows the first flexible tab 53 to cross the projection 55 or tooth 57 in order to give the user a first audible indication such as a "click" and/or tactile indication, due for example to the extra force required to cross the projection 55 or tooth 57.

For example, the bending strength of the first flexible tab 53 is greater than that of the second flexible tab 61, so that user can easily distinguish whether the injection of an implant is almost complete or whether this implant has been injected.

In the example shown, the second rack element 39 comprises two teeth 57, positioned one behind the other so as to correspond to the injection of a first implant then of a second implant. Thus, the first tooth 57, positioned downstream from the second tooth 57, cooperates with the second tab 61 then the first tab 53 when injecting a first implant, and the second tooth 57 cooperates with the second tab 61 then the first tab 53 when injecting a second implant.

Figure 5:
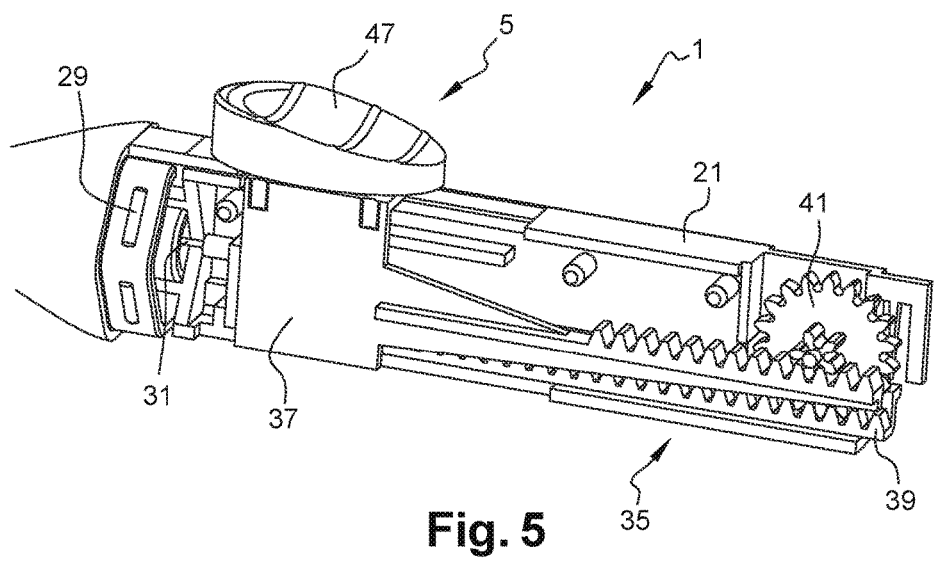
FIGS. 5 to 7 are side and perspective views of a part of the implant injection device of FIG. 1, in which the pushing rod is in a final position.

Lastly, when the pushing rod 31 reaches its final position, as shown on FIGS. 5 and 6, it projects towards the downstream direction past the end of the injection needle 9. In this position, the male support element 21 forms an abutment for the second rack element 39. In this position, the implants are all injected.

The invention is not limited to the embodiments described and other embodiments will be clearly apparent to those skilled in the art. Although the invention has been illustrated with an implant injection device 1, configured to inject two implants, those skilled in the art will easily understand that such an implant injection device 1 can be configured to inject a single implant, for example very long, or more than two implants.

What is claimed is:

1. An implant injection device, comprising:
   an injection needle carried by a gripping unit,
   a receiver housing for receiving at least one implant,
   an injection mechanism comprising:
      a pushing rod, arranged upstream from the at least one implant housed in the receiver housing, extending longitudinally and configured to push the at least one implant through the injection needle between an initial position and a final position in which the at least one implant is injected,
   an actuation mechanism configured to actuate a displacement of the pushing rod by a user from the initial position to the final position, the actuation mechanism comprising a rack transmission mechanism, wherein the rack transmission mechanism comprises a first rack element and a second rack element, a locking mechanism arranged to block the pushing rod in the final position, in which the pushing rod projects towards a downstream direction past an end of the injection needle, wherein the locking mechanism prevents the implant injection device from being reused, and wherein the locking mechanism comprises a lug supported by one of the first rack element and the second rack element, wherein the lug cooperates with a recess carried by the gripping unit.

2. The implant injection device according to claim 1, wherein the first rack element is configured to be driven by the user and forming a first rack and pinion type link with a pinion, the pinion comprising a first set of gear teeth cooperating with the first rack element, the pinion comprising a second set of gear teeth cooperating with the second rack element, configured to push the pushing rod from the initial position to the final position.

3. The implant injection device according to claim 2, wherein the actuation mechanism comprises an actuation button sliding in a direction substantially parallel to a longitudinal direction of the pushing rod, which is supported by the first rack element.

4. The implant injection device according to claim 2, wherein the pinion is pivotally mounted on the gripping unit.

5. The implant injection device according to claim 2, wherein a number of teeth of the first set of gear teeth is strictly less than a number of teeth of the second set of gear teeth.

6. The implant injection device according to claim 1, comprising an indicator for indicating a position of the pushing rod to the user.

7. The implant injection device according to claim 6, wherein the indicator comprises a first flexible tab carried by the gripping unit, and the rack transmission mechanism comprising at least one projection, such that when the rack transmission mechanism reaches a first predetermined position, the at least one projection is in abutment against the first flexible tab to give the user a first audible and/or tactile indication.

8. The implant injection device according to claim 7, wherein the indicator comprises a second flexible tab carried by the gripping unit, the second flexible tab being configured to abut against the at least one projection in a second predetermined position preceding the first predetermined position, such that when the rack transmission mechanism reaches the second predetermined position, the at least one projection is in abutment against the second flexible tab, and when the rack transmission mechanism goes past the second predetermined position, the second flexible tab crosses the at least one projection in order to give the user a second audible and/or tactile indication.

9. The implant injection device according to claim 8, wherein a bending strength of the first flexible tab is greater than a bending strength of the second flexible tab.

10. The implant injection device according to claim 7, wherein the receiver housing is adapted to receive the at least one implant comprising a plurality of implants, and the pushing rod, in the first predetermined position of the rack transmission mechanism, occupies a position in which an implant of the at least one implant comprising the plurality of implants is injected.

11. The implant injection device according to claim 7, wherein the at least one projection comprises a tooth protruding from a flat longitudinal surface of the rack transmission mechanism.

\* \* \* \* \*